US007115361B2

(12) United States Patent
Lalvani et al.

(10) Patent No.: US 7,115,361 B2
(45) Date of Patent: Oct. 3, 2006

(54) DETECTION OF CD8+ T CELL RESPONSES TO *M. TUBERCULOSIS*

(75) Inventors: Ajit Lalvani, Oxford (GB); Ansar A. Pathan, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 10/721,798

(22) Filed: Nov. 26, 2003

(65) Prior Publication Data
US 2004/0141985 A1    Jul. 22, 2004

Related U.S. Application Data

(60) Division of application No. 09/916,201, filed on Jul. 27, 2001, now abandoned, which is a continuation-in-part of application No. 09/467,893, filed on Dec. 21, 1999, now abandoned.

(60) Provisional application No. 60/113,783, filed on Dec. 23, 1998.

(51) Int. Cl.
*C12Q 1/00* (2006.01)
*C12N 5/00* (2006.01)
*A61K 49/00* (2006.01)

(52) U.S. Cl. .............................. 435/4; 424/9.1; 424/9.2; 424/184.1; 424/185.1; 435/325; 435/363; 435/372; 435/374; 436/501; 530/300; 530/350

(58) Field of Classification Search ................ 424/9.1, 424/9.2, 184.1, 185.1; 435/325, 363, 372, 435/374, 4; 436/501; 530/300, 350
See application file for complete search history.

(56) References Cited

U.S. PATENT DOCUMENTS

| 5,955,077 A * | 9/1999 | Andersen et al. ........ 424/184.1 |
| 2002/0131976 A1 | 9/2002 | Lalvani et al. |
| 2002/0136733 A1 | 9/2002 | Hill et al. |
| 2004/0058399 A1 | 3/2004 | Lalvani |
| 2004/0141985 A1 | 7/2004 | Lalvani et al. |

FOREIGN PATENT DOCUMENTS

| WO | WO 95/01441 | 1/1995 |
| WO | WO 98/23960 | 6/1998 |

OTHER PUBLICATIONS

Flynn et al, "Major histocompatibility complex class I-restricted T cells are required for resistance to *Mycobacterium tuberculosis* infection", Proc. Natl. Acad. Sci. USA 89:12013-12017 (1992).
Silva et al, "Protection against tuberculosis by passive transfer with T-cell clones recognizing mycobacterial heat-shock protein 65", Immunology 83:341-346 (1994).
Müller et al, "Impaired Resistance to *Mycobacterium tuberculosis* Infection after Selective In Vivo Depletion of L3T4+ and Lyt-2+ T Cells", Infection and Immunity 55(9):2037-2041 (1987).
Orme and Collins, "Adoptive Protection of the *Mycobacterium tuberculosis*-Infected Lung", Cellular Immunology 84:113-120 (1984).
Turner and Dockrell, "Stimulation of human peripheral blood mononuclear cells with live *Mycobacterium bovis* BCG activates $CD8^+$ T cells *in vitro*", Immunology 87:339-342 (1996).
Horwitz et al, "Protective immunity against tuberculosis induced by vaccination with major extracellular proteins of *Mycobacterium tuberculosis*", Proc. Natl. Acad. Sci. USA 92:1530-1534 (1995).
Andersen et al, "Recall of Long-Lived Immunity to *Mycobacterium tuberculosis* Infection in Mice", J. Immunol. 154:3359-3372 (1995).
DeLibero et al, "Mycobacteria-reactive $Lyt-2^+$ T cell lines", Eur. J. Immunol. 18:59-66 (1988).
Lalvani et al, "Human cytolytic and interferon γ-secreting $CD8^+$ T lymphocytes specific for *Mycobacterium tuberculosis*", Proc. Natl. Acad. Sci. USA 95:270-275 (1998).
Tan et al, "Human Alveolar T Lymphocyte Responses to Mycobacterium tuberculosis Antigens", J. Immunol. 159:290-297 (1997).
Brandt et al, "Key Epitopes on the ESAT-6 Antigen Recognized in Mice During the Recall of Protective Immunity to *Mycobacterium tuberculosis*", The Journal of Immunology 157:3527-3533 (1996).
Sørensen et al, "Purification and Characterization of a Low-Molecular-Mass T-Cell Antigen Secreted by *Mycobacterium tuberculosis*", Infection and Immunity 63(5):1710-1717 (1995).
Geluk et al, "Identification of Major Epitopes of *Mycobacterium tuberculosis* AG85B That Are Recognized by HLA-A*0201-Restricted CD8+ T Cells in HLA-Transgenic Mice and Humans", The Journal of Immunology 165:6463-6471 (2000).

(Continued)

Primary Examiner—Rodney P Swartz
(74) Attorney, Agent, or Firm—Nixon & Vanderhye P.C.

(57) ABSTRACT

A method of detecting an anti-mycobacterial CD8 T cell response comprising contacting a population of CD8 T cells of an individual with one or more peptides selected from the peptides represented by SEQ ID NO: 3, 4, 7, 8, 9, 10, 11 or 12, and, optionally, one or two further peptides represented by SEQ ID NO: 1 and/or 2, wherein one or more of said peptides may be substituted by an analogue which binds a T cell receptor which recognises the corresponding substituted peptide, and determining whether CD8 T cells of the CD8 T cell population recognize the peptide(s).

The invention also provides a method of vaccinating against infection by a *mycobacterium*, wherein the vaccination leads to a CD8 T cell response, comprising administering (i) a CD8 T cell epitope of a *mycobacterium* protein, (ii) an analogue of the epitope which is capable of inhibiting the binding of the epitope to a T cell receptor, (iii) a precursor or (i) or (ii) which is capable of being processed to provide (i) or (ii), or (iv) a polynucleotide which is capable of being expressed to provide (i), (ii) or (iii).

18 Claims, 4 Drawing Sheets

OTHER PUBLICATIONS

Lewinsohn et al, "Classically Restricted Human CD8+ T Lymphocytes Derived from *Mycobacterium tuberculosis*-Infected Cells: Definition of Antigenic Specificity", The Journal of Immunology 166:439-446 (2001).

Smith et al, "Human CD8+ CTL Specific for the Mycobacterial Major Secreted Antigen 85A[1]", The Journal of Immunology 165:7088-7095 (2000).

Klein et al, "HLA-B*35-Restricted CD8 T Cell Epitopes in the Antigen 85 Complex of *Mycobacterium tuberculosis*", J. Infectious Diseases 183:928-934 (2001).

Mohagheghpour et al, "CTL Response to *Mycobacterium tuberculosis*: Identification of an Immunogenic Epitope in the 19-kDa Lipoprotein[1]", The Journal of Immunology 161:2400-2406 (1998).

Pathan et al, "High frequencies of circulating IFN-γ-secreting CD8 cytotoxic T cells specific for a novel MHC class I-restricted *Mycobacterium tuberculosis* epitope in *M. tuberculosis*-infected subjects without disease", Eur. J. Immunol. 30:2713-2721 (2000).

Wiegeshaus and Smith, "Evaluation of the Protective Potency of New Tuberculosis Vaccines", Reviews of Infectious Diseases 11 (Suppl 2):S484-S490 (1989).

Lalvani and Hill, "Cytotoxic T-lymphocytes against malaria and tuberculosis: from natural immunity to vaccine design", Clinical Science 95:531-538 (1998).

Pollock and Andersen, "The Potential of the ESAT-6 Antigen Secreted by Virulent Mycobacteria for Specific Diagnosis of Tuberculosis", The Journal of Infectious Diseases 175:1251-1254 (1997).

U.S. Appl. No. 09/308,725, filed May 24, 1999.

Laurens et al, "Control of latent *Mycobacterium tuberculosis* infection is dependent on CD8 T cells", Eur. J. Immunol. 30:3689-3698 (2000).

Kamath et al, "Differential Protective Efficacy of DNA Vaccine Expressing Secreted Proteins of *Mycobacterium tuberculosis*", Infection and Immunity 67(4):1702-1707 (1999).

Tascon et al, "Protection against *Mycobacterium tuberculosis* Infection by CD8+ T Cells Requires the Production of Gamma Interferon", Infection and Immunity 66(2):830-834 (1998).

Behar et al, "Susceptibility of Mice Deficient in CD1D or TAP1 to Infection with *Mycobacterium tuberculosis*", J. Exp. Med. 189(12):1973-1980 (1999).

Smith et al, Human CD8+ CTL Specific for the Mycobacterial Major Secreted Antigen 85A, The Journal of Immunology 165:7088-7095 (2000).

Cho et al, "Antimicrobial activity of MHC class I-restricted CD8+ T cells in human tuberculosis", Proc. Natl. Acad. Sci. USA 97(22):12210-12215 (2000).

Dillion et al, "Molecular Characterization and Human T-Cell Responses to a Member of a Novel *Mycobacterium tuberculosis* mtb39 Gene Family", Infection and Immunity 67(6):2941-2950 (1999).

Wilkinson et al, "38000 MW antigen-specific major histocompatibility complex class I restricted interferon-γ-secreting CD8+ T cells in healthy contacts of tuberculosis", Immunology 95:585-590 (1998).

Tanghe et al, "Improved Immunogenicity and Protective Efficacy of a Tuberculosis DNA Vaccine Encoding Ag85 by Protein Boosting", Infection and Immunity 69(5):3041-3047 (2001).

Malin et al, "Vaccinia expression of *Mycobacterium tuberculosis*-secreted proteins: tissue plasminogen activator signal sequence enhances expression and immunogenicity of *M. tuberculosis* Ag85", Microbes and Infection 2:1677-1685 (2000).

Wang et al, Induction of CD4+ T cell-dependent CD8+ tuype 1 responses in human by a malaria DNA vaccine, Proc. Natl. Acad. Sci. USA 98(19):10817-10822 (2001).

Wang et al, "Induction of Antigen-Specific Cytotoxic T Lymphocytes in Humans by a Malaria DNA Vaccine", Science 282:476-480 (1998).

Roy et al, "Induction of antigen-specific CD8+ T cells, T helper cells, and protective levels of antibody in humans by particle-mediated administration of a hepatitis B virus DNA vaccine", Vaccine 19:764-778 (2001).

Cao et al, "Immunogenicity of a Recombinant Human Immunodeficiency Virus (HIV)-Canarypox Vaccine in HIV-Seronegative Ugandan Volunteers: Results of the HIV Network for Prevention Trials007 Vaccine Study", The Journal of Infectious Diseases 187:887-895 (2003).

McShane et al, "Protective Immunity against *Mycobacterium tuberculosis* Induced by Dendritic Cells Pulsed with both CD8+-and CD4+-T-cell Epitopes from Antigen 85A", Infection and Immunity 70(3):1623-1626 (2002).

* cited by examiner

DETECTION OF CD8+ T CELL RESPONSES TO *M. TUBERCULOSIS*

This application is a divisional of application Ser. No. 09/916,201, filed Jul. 27, 2001, now abandoned, which is a continuation-in-part of application Ser. No. 09/467,893, filed Dec. 21, 1999, now abandoned, which claims benefit of Provisional Application No. 60/113,783, filed Dec. 23, 1998, the entire contents of which are hereby incorporated by reference in this application.

FIELD OF THE INVENTION

The invention relates to a method of detecting an anti-mycobacterial CD8 T cell response and a method of vaccination against mycobacterial infection using peptides and proteins containing mycobacterial CD8 T cell epitopes. The *mycobacterium* may be *M. tuberculosis*.

BACKGROUND OF THE INVENTION

The current live attenuated vaccine for tuberculosis, BCG, has variable and limited efficacy in tuberculosis-endemic regions. For a vaccine to be effective it must cause the generation of a strong immune response against *M. tuberculosis*. Until now researchers in this field have concentrated on CD4 T cell and antibody responses to *M. tuberculosis*. A correlation has not been shown in humans between infection with *M. tuberculosis* and the generation of a CD8 T cell response against specific *M. tuberculosis* antigens.

SUMMARY OF THE INVENTION

Using an assay which detects release of IFN-γ from T cells, the inventors have shown that CD8 T cells specific for tuberculosis antigens exist during tuberculosis infection and have identified particular CD8 T cell epitopes from ESAT-6 which are recognized. Such epitopes may be used to detect anti-mycobacterial CD8 T cells. The inventors have also shown the presence of CD8 T cells specific for tuberculosis antigens in healthy contacts suggesting that such cells may be protective against tuberculosis.

Accordingly the invention provides a method of detecting an anti-mycobacterial CD8 T cell response comprising contacting a population of CD8 T cells of an individual with one or more peptides selected from the peptides of SEQ ID NOS: 3, 4, 7, 8, 9, 10, 11 and 12, and, optionally, one or two further peptides of SEQ ID NOS: 1 and/or 2, wherein one or more of said peptides may be substituted by an analogue which binds a T cell receptor that recognizes the peptide, and determining whether CD8 T cells of the CD8 T cell population recognize the peptide(s).

The invention also provides a method of vaccinating against infection by a *mycobacterium*, wherein the vaccination leads to a CD8 T cell response, comprising administering (i) a CD8 T cell epitope of a *mycobacterium* protein, (ii) an analogue of the epitope which is capable of inhibiting the binding of the epitope to a T cell receptor, (iii) a precursor of (i) or (ii) which is capable of being processed to provide (i) or (ii), or (iv) a polynucleotide which is capable of being expressed to provide (i), (ii) or (iii).

DETAILED DESCRIPTION OF THE INVENTION

Figure 1:
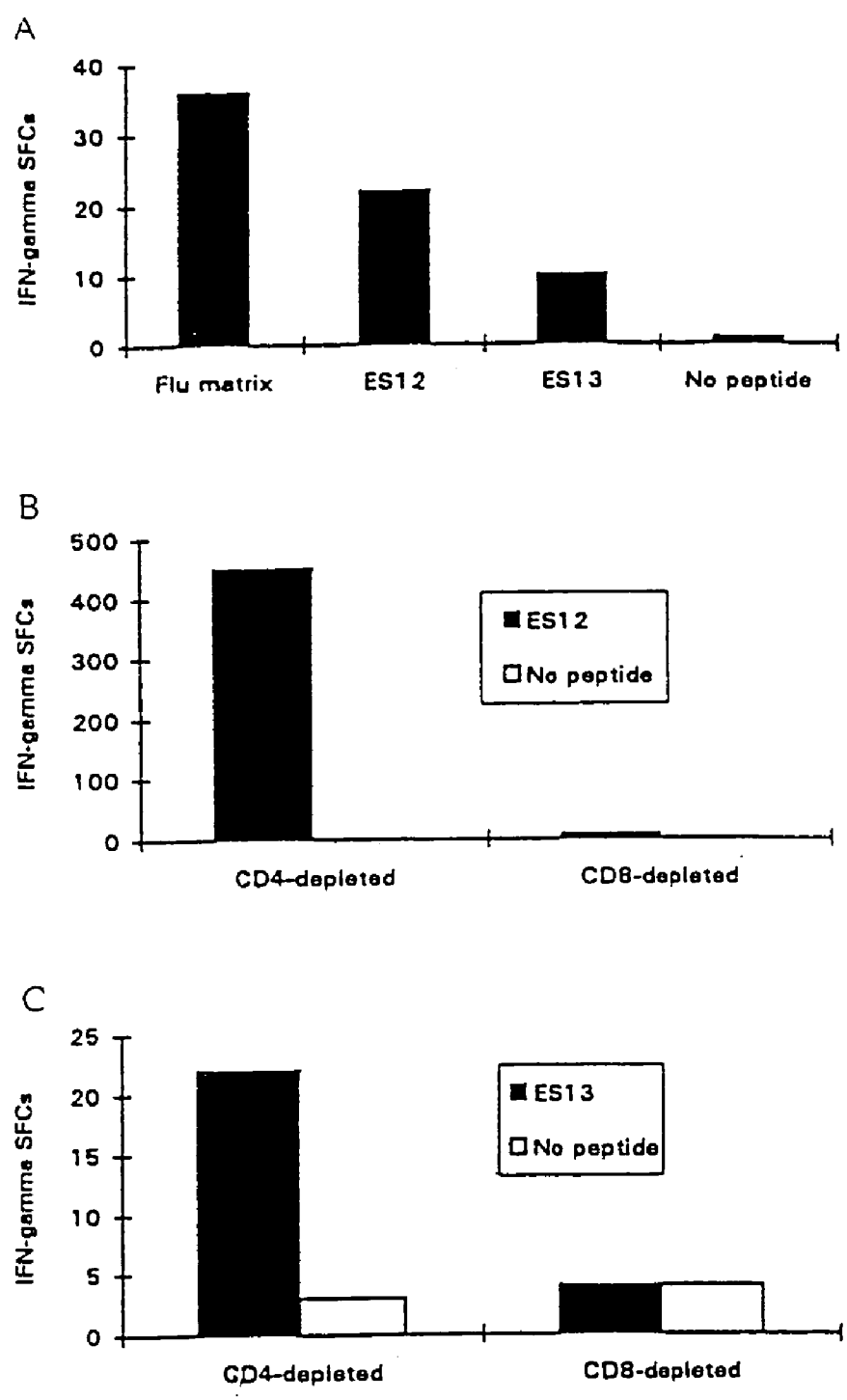
FIG. 1(A) shows numbers of circulating peptide-specific effectors from peripheral blood of NPH54.
FIG. 1(B) shows that peptide G specific IFN-γ secreting T cells are CD8+.
FIG. 1(C) shows peptide E specific IFN-γ release by an STCL.

The term "epitope" as used herein includes analogues of the epitope, unless the context requires otherwise. It is understood that the term "peptide" as used herein also includes the analogue of that peptide (which may not be a peptide as defined by the ordinary use of the term) unless the context requires otherwise.

The invention provides a method of detecting anti-mycobacterial CD8 T cell responses in an individual. This may be done for the purpose of testing the efficacy of a vaccine or for the purpose of diagnosing a mycobacterial infection. The invention also provides a method of vaccination of an individual.

The sequences of SEQ ID NO's 1 to 12 are shown below:

```
SEQ ID NO:1-AMASTEGNV
SEQ ID NO:2-LQNLARTI
SEQ ID NO:3-NVTSIHSLL
SEQ ID NO:4-ELNNALQNLART
SEQ ID NO:5-TATELNNALQNLART
SEQ ID NO:6-NLARTISEAGQAMAS
SEQ ID NO:7-SGSEAYQGVQQKWDA
SEQ ID NO:8-TATELNNAL
SEQ ID NO:9-RTISEAGQAM
SEQ ID NO:10-AYQGVQQKW
SEQ ID NO:11-SEAYQGVQQ
SEQ ID NO:12-SEAYQGVQQK
```

SEQ ID NO's 1 to 4 and 8 to 10 are the minimal epitopes which are recognised by CD8 T cells. SEQ ID NO's 8 to 10 represent minimal epitopes which are present in the peptides SEQ ID NO's 5 to 7 respectively. In addition another CD8 T cell epitope is present in SEQ ID NO:7. The identity of the additional epitope is still under investigation but is likely to be one the peptides represented by SEQ ID NO's 11 and 12.

The Individual in whom a CD8 T Cell Response is Detected or who is Vaccinated

The individual is generally a mammal, such as a human or animal, typically one which can be naturally or artificially infected by a *mycobacterium*. The individual may be a primate, cow, sheep, pig, badger or rodent (e.g. a mouse or rat). The individual may test positive or negative in a Mantoux test. The individual may be at risk of a mycobacterial infection, typically for socio-economic reasons or may have a genetic or acquired predisposition to mycobacterial infection.

In the method of detecting an anti-mycobacterial CD8 T cell response the individual has preferably been vaccinated with a vaccine intended to provided protection against a mycobacterial infection. The vaccine generally comprises proteins comprising mycobacterial sequence. The vaccine may comprise any of the polypeptides, polynucleotides or compositions discussed herein. The vaccination will generally have taken place within a year before the method is carried out, for example within six months or within a month before the method is carried out.

The Epitope Used in the Detection or Vaccination Method

The epitope which is used in the detection method or vaccination is of a *mycobacterium* protein. Such a *mycobacterium* is typically pathogenic and capable of infecting mammals, such as those mammals discussed above. The *mycobacterium* is typically *M. tuberculosis*, but may also be *M. marinum*, *M. kansasii* or *M. bovis*.

The *mycobacterium* protein containing the epitope is typically one which is secreted from the *mycobacterium*, and is preferably ESAT-6. Such an ESAT-6 protein is generally homologous to ESAT-6 of *M. tuberculosis*.

The epitope used may be selected from the minimal epitopes represented by or present in any one of SEQ ID NOS: 1 to 12.

The Detection Method

The CD8 T cells which recognize the peptide in the detection method have generally been presensitized in vivo to antigen from a vaccine or from a *mycobacterium* infection. These antigen-experienced T cells are generally present in the peripheral blood of a host which has been exposed to the antigen at a frequency of 1 to $10^6$ to 1 in $10^3$ peripheral blood mononuclear cells (PBMCs).

In the method the T cells can be contacted with the peptides in vitro or in vivo, and determining whether the T cells recognise the peptide can be done in vitro or in vivo.

Determination of whether the T cells recognize the peptide is generally done by detecting a change in the state of the T cells in the presence of the peptide or determining whether the T cells bind the peptide. The change in state is generally caused by antigen specific functional activity of the T cell after the T cell receptor binds the peptide. Generally when binding the T cell receptor the peptide is bound to an MHC class I molecule, which may be present on the surface of a PBMC or an antigen presenting cell (APC).

The change in state of the T cell may be the start of or increase in secretion of a substance from the T cell, such as a cytokine, especially IFN-γ, IL-2 or TNF-α. Determination of IFN-γ secretion is particularly preferred. The substance can typically be detected by allowing it to bind to a specific binding agent and then measuring the presence of the specific binding agent/substance complex. The specific binding agent is typically an antibody, such as polyclonal or monoclonal antibodies. Antibodies to cytokines are commercially available, or can be made using standard techniques.

Typically the specific binding agent is immobilized on a solid support. After the substance is allowed to bind the solid support can optionally be washed to remove material which is not specifically bound to the agent. The agent/substance complex may be detected by using a second binding agent which will bind the complex. Typically the second agent binds the substance at a site which is different from the site which binds the first agent. The second agent is preferably an antibody and is labelled directly or indirectly by a detectable label.

Thus the second agent may be detected by a third agent which is typically labelled directly or indirectly by a detectable label. For example the second agent may comprise a biotin moiety, allowing detection by a third agent which comprises a streptavidin moiety and typically alkaline phosphatase as a detectable label.

In one embodiment the detection system which is used is the ex-vivo ELISPOT assay described in WO 98/23960. In that assay IFN-γ secreted from the T cell is bound by a first IFN-γ specific antibody which is immobilised on a solid support. The bound IFN-γ is then detected using a second IFN-γ specific antibody which is labelled with a detectable label. Such a labelled antibody can be obtained from MABTECH (Stockholm, Sweden). Other detectable labels which can be used are discussed below. The ELISPOT assay may be used with freshly isolated T cells.

The change in state of the T cell which can be measured may be the increase in the uptake of substances by the T cell, such as the uptake of thymidine. The change in state may be an increase in the size of the T cells, or proliferation of the T cells, or a change in cell surface markers on the T cell.

Generally the T cells which are used in the method are taken from the host in a blood sample, although other types of samples which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T cells and APCs. Thus in the method the APCs present in the separated MCs can present the peptide to the T cells. In another embodiment only T cells, such as only CD8 T cells, can be purified from the sample. PBMCs, MCs and T cells can be separated from the sample using techniques known in the art, such as those described in (2).

In one embodiment the T cells used in the assay are in the form of unprocessed or diluted samples, or are preferably freshly isolated T cells (such as in the form of freshly isolated MCs or PBMCs) which are used directly ex vivo, i.e. they are not cultured before being used in the method. However the T cells can be cultured before use, for example in the presence of one or more of the peptides, and generally also exogenous growth promoting cytokines. During culturing the peptides are typically present on the surface of cells such as APCs. Pre-culturing of the T cells may lead to an increase in the sensitivity of the method. Thus the T cells can be converted into cell lines, such as short term cell lines (for example as described in (4)).

The APC used in the method may be any cell which has MHC class I molecules on its surface. It may or may not be a specialized antigen presenting cell, such as a B cell, dendritic cell or macrophage. The APC used in the method may be from the same host as the T cell or from a different host. The APC may be a naturally occurring APC or an artificial APC. The APC is capable of presenting the peptide to a T cell. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalized cell line.

Typically in the method the T cells derived from the sample can be placed into an assay with all the peptides (i.e. a pool of the peptides) which it is intended to test the relevant panel or the T cells can be divided and placed into separate assays each of which contain one or more of the peptides. In the in vivo embodiment of the detection method the relevant peptide(s) will of course be administered to the host. Typically one or more, or all, of the peptides of SEQ ID NOS: 3, 4, 8, 9 and 10 are also used in the method. In another embodiment only the peptides of SEQ ID NOS: 1,2,3,4,8,9, 10 and one of 11 or 12 are used in the method.

The invention also provides the peptides such as two or more of any of the peptides mentioned herein (for example in any of the combinations mentioned herein) for simultaneous, separate or sequential use.

In one embodiment peptide perse is added directly to an assay comprising T cells and APCs. As discussed above the T cells and APCs in such an assay could be in the form of MCs. When peptides which can be recognized by the T cell without the need for presentation by APCs are used then APCs are not required. Analogues which mimic the original peptide bound to a MHC molecule are an example of such a peptide.

In one embodiment the peptide is provided to the presenting cell in the absence of the T cell. This cell is then provided to the T cell, typically after being allowed to present the peptide on its surface. The peptide may have been taken up inside the cell and presented, or simply be taken up onto the surface without entering inside the cell.

The duration for which the peptide is contacted with the T cells will vary depending on the method used for determining recognition of the peptide. Typically $10^5$ to $10^7$, preferably $5 \times 10^5$ to $10^6$ PBMCs are added to each assay. In the case where peptide is added directly to the assay its concentration is typically from $10^{-1}$ to $10^3$ μg/ml, preferably 0.5 to 50 μg/ml or 1 to 10 μg/ml.

Typically the length of time for which the T cells are incubated with the peptide is from 4 to 24 hours, preferably 6 to 16 hours. When using ex vivo PBMCs it has been found that $0.3 \times 10^6$ PBMCs can be incubated in 10 μg/ml of peptide for 12 hours at 37° C.

The determination of the recognition of the peptide by the T cells may be done by measuring the binding of the peptide to the T cells. Typically T cells which bind the peptide can be sorted based on this binding, for example using a FACS technique. The detection of the presence of T cells which recognise the peptide will be deemed to occur if the frequency of cells sorted using the peptide is above a 'control' value. The frequency of antigen-experienced T cells is generally 1 in $10^6$ to 1 in $10^3$, and therefore whether or not the sorted cells are antigen-experienced T cells can be determined.

The determination of the recognition of the peptide by the T cells may be measured in vivo. Typically the peptide is administered to the individual and then a response which indicates recognition of the peptide may be measured. In one embodiment the peptide is administered intradermally, typically in a similar manner to the Mantoux test. The peptide may be administered epidermally. The peptide is typically administered by needle, such as by injection, but can be administered by other methods such as ballistics, for example the ballistics techniques which have been used to deliver nucleic acids. EP-A-0693119 describes techniques which can typically be used to administer the peptide. Typically from 0.001 to 1000 μg, for example from 0.01 to 100 μg or 0.1 to 10 μg of peptide is administered.

Alternatively an agent can be administered which is capable of providing the peptides in vivo. Thus a polynucleotide capable of expressing the peptide can be administered, typically in any of the ways described above for the administration of the peptide. The polynucleotide typically has any of the characteristics of the polynucleotide which is discussed below. Peptide is expressed from the polynucleotide in vivo and recognition of the peptide in vivo may be measured. Typically from 0.001 to 1000 μg, for example from 0.01 to 100 μg or 0.1 to 10 μg of polynucleotide is administered.

The Vaccination Method

As discussed above in the method of vaccination a CD8 T cell epitope, an analogue of the epitope, a precursor which may be processed to provide the epitope or analogue, or a polynucleotide which is capable of being expressed to provide the epitope, analogue or precursor is administered.

The precursor may comprise the sequence of or be the same as the sequence of a *mycobacterium* protein or a fragment of such a protein. Such a fragment is typically at least 8 amino acids long, for example 9, 10, 11, 12 amino acids long, such as at least 20, 30, 50 or 80 amino acids long. The precursor may thus comprise sequence N-terminal and/or C-terminal to the sequence of the fragment. The precursor may be a natural protein, a fragment thereof or a non-natural protein. Thus ESAT-6 or a fragment of ESAT-6 may employed in the vaccination.

The precursor is either a peptide or non-peptide or may comprise both peptide and non-peptide portions. The precursor typically comprises 1, 2, 3, 4 or more CD8 epitopes which may be the same or different. Typically 1, 2, 3 or more linkers are present in the peptide separating the epitopes. The linkers may be 1, 2, 3, 4 or more amino acids in length. Thus 1, 2, 3, or more, or all of the epitopes may be contiguous with each other or separated from each other. The precursor is typically 10 to 2000 amino acids in length, such as 50 to 1000, or 200 to 500 amino acids.

The epitope is generally 8, 9, 10, 11, 12 or more amino acids in length and is capable of binding an HLA class I A, B or C molecule, or the equivalents of these molecules in a non-human animal. The epitope is generally able to bind an HLA class I molecule present in the individual or population which is to be vaccinated. The epitope is typically capable of binding HLA-A2, HLA-A11 (e.g. HLA-A11.01), HLA-A68 (e.g. HLA-A68.02), HLA-B7, HLA-B8, HLA-B35, HLA-B52 or HLA-B53 or the equivalent molecules in a non-human animal.

The sequence of the epitope may be any of the sequences of SEQ ID NOS: 1, 2, 3, 4, 8, 9, 10, 11 and 12 or the sequence of an epitope present SEQ ID NO: 7 (other than the SEQ ID NO:10 sequence).

Generally the precursor is capable of being processed by an antigen presenting cell (APC) leading to the presentation of the epitopes bound to an MHC class I molecule on the surface of the APC.

Methods of obtaining T cell responses are known in the art. Generally a CD8 T cell response can be obtained by vaccinating using an appropriate dose, route of administration, adjuvant (e.g. those in (25) or (26)) or delivery system. In one embodiment the delivery system is capable of providing the epitope or precursor to an antigen presenting cell, for example in an intracellular location which allows presentation of the epitope or of epitopes derived from the precursor.

Typically the delivery system comprises the polynucleotide discussed below, for example in the form of a recombinant virus or DNA particles. In one embodiment the epitope, precursor or polynucleotide are provided to an APC (such as any of the types of APCs discussed herein) ex vivo and the APC is then administered to the individual.

The adjuvant may cause the epitope, precursor or polynucleotide to adopt a particulate form. The adjuvant is typically a virus or virus-like particle (such as a yeast Ty particle, e.g. as in (25)), an acrylic based microbead, a saponin (e.g. a 3,28-O-bisglycoside quillaic acid) or an emulsion (e.g. oil in water or water in oil) such as soybean emulsion (e.g as in 26).

The polynucleotide which expresses (i), (ii) or (iii) is typically DNA or RNA, and is single or double stranded. The polynucleotide generally comprises coding sequence that encodes (i), (ii) or (iii). The coding sequence is typically operably linked to a control sequence capable of providing for expression of the polynucleotide. Thus typically the polynucleotide comprises 5' and 3' to the coding sequence sequences which aid expression, such as aiding transcription and/or translation of the coding sequence.

The polynucleotide may be capable of expressing (i), (ii) or (iii) in a prokaryotic and/or eukaryotic cell. The polynucleotide is typically capable of expressing (i), (ii) or (iii) in a mammalian cell, such as in the cells of any of the mammals discussed above. The polynucleotide may be capable of expressing (i), (ii) or (iii) in the cellular vector discussed below.

In one embodiment the polynucleotide is present in a virus or cellular vector, such as a virus which is capable of stimulating a CD8 T cell response, such as a vaccinia virus (e.g. MVA or NYVAC).

The vaccination may be based on the specific epitopes discussed above which are, or contained in, SEQ ID NOS: 1 to 12. Thus the invention also provides a method of vaccination which leads to a CD8 T cell response, the T cells of which are specific for a CD8 epitope which is SEQ ID NO: 1, 2, 3, 4, 8, 9, 10, 11 or 12, or which is present in the sequence of SEQ ID NO:7, comprising administering (i) a CD8 epitope which is SEQ ID NO: 1, 2, 3 or 4, or which is present in the sequences of SEQ ID NO: 5, 6 or 7, (ii) an analogue of the epitope which is capable of inhibiting the binding of the epitope to a T cell receptor, (iii) a precursor of (i) or (ii) which is capable of being processed to provide (i) or (ii) excluding ESAT-6 or fragments of ESAT-6, or (iv) a polynucleotide which is capable of being expressed to provide (i), (ii) or (iii). (iii) may be the peptide of SEQ ID NO: 5, 6 or 7.

The invention also provides these particular epitopes, analogues, precursors and polynucleotides represented by (i), (ii), (iii) and (iv), which may be in a pharmaceutical composition in association with a pharmaceutically acceptable carrier or diluent.

As discussed above particular adjuvants or delivery systems may be used which stimulate a CD8 T cell response. Thus the invention also provides a vaccine comprising an adjuvant which stimulates a CD8 T cell response and any of the epitopes, analogues, precursors or polynucleotides discussed above. The invention also provides these epitopes, analogues, precursors or polynucleotides in association with a delivery system which is capable of stimulating a CD8 T cell response.

Analogues of the Peptides Used in the Detection or Vaccination Method

The analogue of a peptide can bind to a T cell receptor which recognizes the original peptide. Therefore generally when the analogue is added to T cells in the presence of the original peptide, typically also in the presence of a presenting cell, the analogue inhibits the recognition of the original peptide. The binding of the analogue to the said T cell receptors can be tested by standard techniques. Such T cell receptors can be isolated from T cells which have been shown to recognize the peptide (e.g. using the method of the invention). Optionally such T cells may be sorted based on their ability to recognize the original peptide, for example using a FACS technique. Demonstration of the binding of the analogue to the T cell receptors can then shown by determining whether the T cell receptors inhibit the binding of the analogue to a substance that binds the analogue, e.g. an antibody to the analogue. Typically the analogue is bound in an MHC class I molecule in such an inhibition of binding assay.

Typically the analogue inhibits the binding of the peptide to a T cell receptor. In this case the amount of peptide which can bind the T cell receptor in the presence of the analogue is decreased. This is because the analogue is able to bind the T cell receptor and therefore competes with the peptide for binding to the T cell receptor.

T cells for use in the above binding experiments can be isolated from patients with mycobacterial infection or from individual who have been administered with an anti-mycobacterial vaccine (such as any such vaccine mentioned herein). Whole ESAT-6 is not encompassed by the term 'analogue'.

Other binding characteristics of the analogue are also the same as the peptide, and thus typically the analogue binds to the same MHC class I molecule which the peptide binds. The analogue typically binds to antibodies specific for the peptide, and thus inhibits binding of the peptide to such an antibody.

The analogue is typically a peptide. It may have homology with the original peptide. The analogue is typically at least 70% homologous to the original peptide, preferably at least 80 or 90% homologous thereto, over the entire length of the original peptide. Methods of measuring protein homology are well known in the art and it will be understood by those of skill in the art that in the present context, homology is calculated on the basis of amino acid identity (sometimes referred to as "hard homology") For example the UWGCG Package provides the BESTFIT program which can be used to calculate homology (for example used on its default settings) (1).

The analogue may differ (be derived) from the original peptide by substitution, insertion or deletion, for example by 1, 2, 3, 4 or more substitutions, deletions or insertions. The substitutions are preferably 'conservative'. These are defined according to the following Table. Amino acids in the same block in the second column and preferably in the same line in the third column may be substituted for each other:

| ALIPHATIC | Non-polar | G A P |
| | | I L V |
| | Polar - uncharged | C S T M |

-continued

| | | |
|---|---|---|
| | Polar - charged | N Q<br>D E<br>K R |
| AROMATIC | | H F W Y |

The analogue typically has a length of 8, 9, 10, 11 or 12 amino acids. Typically the amino acids in the analogue at the equivalent positions to amino acids in the original peptide which contribute to binding the MHC molecule or are responsible for the recognition by the T cell receptor, are the same or are conserved.

Typically the analogue peptide comprises one or more modifications, which may be natural post-translation modifications or artificial modifications. The modification may provide a chemical moiety (typically by substitution of a hydrogen, e.g. of a C—H bond), such as an amino, acetyl, hydroxy or halogen (e.g. fluorine) group or carbohydrate group. Typically the modification is present on the N or C terminus.

The analogue may comprise one or more non-natural amino acids, for example amino acids with a side chain different from natural amino acids. Generally, the non-natural amino acid will have an N terminus and/or a C terminus. The non-natural amino acid may be an L- or D-amino acid.

The analogue typically has a shape, size, flexibility or electronic configuration which is substantially similar to the original peptide. It is typically a derivative of the original peptide.

In one embodiment the analogue is or mimics the original peptide bound to a MHC class I molecule. The analogue may be or may-mimic the original peptide bound to 2, 3, 4 or more MHC class I molecules associated or bound to each other. These MHC molecules may be bound together using a biotin/streptavidin based system, in which typically 2, 3 or 4 biotin labelled MHC molecules bind to a streptavidin moiety. This analogue typically inhibits the binding of the peptide/MHC Class I complex to a T cell receptor or antibody which is specific for the complex.

The analogue is typically an antibody or a fragment of an antibody, such as a Fab or (Fab)$_2$ fragment.

The analogue may be immobilized on a solid support, particularly an analogue which mimics peptide bound to a MHC molecule.

The analogue is typically designed by computational means and then synthesized using methods known in the art. Alternatively the analogue can be selected from a library of compounds. The library may be a combinatorial library or a display library, such as a phage display library. The library of compounds may be expressed in the display library in the form of being bound to a MHC class I molecule, such as the MHC molecule which the original peptide binds. Analogues are generally selected from the library based on their ability to mimic the binding characteristics of the original peptides. Thus they may be selected based on ability to bind a T cell receptor or antibody which recognizes the original peptide.

Kits Provided by the Invention

The invention also provides a kit for carrying out the method comprising one or more of the peptides or analogues and optionally a means to detect the recognition of the peptide by the T cell. Typically the means to detect recognition allows or aids detection based on the techniques discussed above.

Thus the means may allow detection of a substance secreted by the T cells after recognition. The kit may thus additionally include a specific binding agent for the substance, such as an antibody. The agent is typically specific for IFN-γ. The agent is typically immobilized on a solid support This means that after binding the agent the substance will remain in the vicinity of the T cell which secreted it. Thus 'spots' of substance/agent complex are formed on the support, each spot representing a T cell which is secreting the substance. Quantifying the spots, and typically comparing against a control, allows determination of recognition of the peptide.

The kit may also comprise a means to detect the substance/agent complex. A detectable change may occur in the agent itself after binding the substance, such as a colour change. Alternatively a second agent directly or indirectly labelled for detection may be allowed to bind the substance/agent complex to allow the determination of the spots. As discussed above the second agent may be specific for the substance, but binds a different site on the substance than the first agent.

The immobilized support may be a plate with wells, such as a microtitre plate. Each assay can therefore be carried out in a separate well in the plate.

The kit may additionally comprise medium for the T cells, detection agents or washing buffers to be used in the detection steps. The kit may additionally comprise reagents suitable for the separation from the sample, such as the separation of PBMCs or T cells from the sample. The kit may be designed to allow detection of the T cells directly in the sample without requiring any separation of the components of the sample.

The kit may comprise an instrument which allows administration of the peptide, such as intradermal or epidermal administration. Typically such an instrument comprises one or more needles. The instrument may allow ballistic delivery of the peptide. The peptide in the kit may be in the form of a pharmaceutical composition.

The kit may also comprise controls, such as positive or negative controls. The positive control may allow the detection system to be tested. Thus the positive control typically mimics recognition of the peptide in any of the above methods. Typically in the kits designed to determine recognition in vitro the positive control is a cytokine. In the kit designed to detect in vivo recognition of the peptide the positive control may be antigen to which most individuals should response.

The kit may also comprise a means to take a sample containing T cells from the host, such as a blood sample. The kit may comprise a means to separate mononuclear cells or T cells from a sample from the host.

Peptide, Polynucleotides and Antibodies Provided by the Invention

The invention also provides a peptide whose sequence is any one of SEQ ID NOS: 3, 4, 5, 6, 7, 8, 9, 10, 11 and 12 or an analogue thereof. The invention provides a diagnostic product or panel comprising one or more of these peptides typically in the combinations discussed above. Such a product is typically a composition such as a pharmaceutical composition.

The invention also provides a polynucleotide which is capable of expression to provide a peptide comprising the sequence of SEQ ID NO: 1, 2, 3, 4, 5, 6, 7, 8, 9, 10, 11 or 12; or an analogue thereof. Typically the polynucleotide is DNA or RNA, and is single or double stranded. The polynucleotide therefore comprises sequence which encodes the sequence of SEQ ID NO: 1, 2, 3, 4, 5, 6, 7, 8, 9, 10, 11 or 12. To the 5' and 3' of this coding sequence the polynucleotide of the invention has sequence or codons which are different from the sequence or codons 5' and 3' to these sequences in the ESAT-6 gene. Therefore the polynucleotide of the invention does not comprise the sequence coding for the whole of ESAT-6 or fragments of ESAT-6, other than sequences coding for fragments of SEQ ID NO: 1, 2, 3, 4, 5, 6, 7, 8, 9, 10, 11 and 12.

5' and/or 3' to the sequence encoding the peptide the polynucleotide has coding or non-coding sequence. Sequence 5' and/or 3' to the coding sequence may comprise sequences which aid expression, such as transcription and/or translation, of the sequence encoding the peptide. The polynucleotide may be capable of expressing the peptide in a prokaryotic or eukaryotic cell. In one embodiment the polynucleotide is capable of expressing the peptide in a mammalian cell, such as a human, primate or rodent cell.

The polynucleotide may be incorporated into a replicable vector. Such a vector is able to replicate in a suitable cell. The vector may be an expression vector. In such a vector the polynucleotide of the invention is operably linked to a control sequence which is capable of providing for the expression of the polynucleotide. The vector may contain a selectable marker, such as the ampicillin resistance gene.

The polynucleotide, peptide or antibody (see below) of the invention, or the agents used in the method (for example in the detection of substances secreted from T cells) may carry a detectable label. Detectable labels which allow detection of the secreted substance by visual inspection, optionally with the aid of an optical magnifying means, are preferred. Such a system is typically based on an enzyme label which causes colour change in a substrate, for example alkaline phosphatase causing a colour change in a substrate. Such substrates are commercially available, e.g. from BioRad. Other suitable labels include other enzymes such as peroxidase, or protein labels, such as biotin; or radioisotopes, such as $^{32}P$ or $^{35}S$. The above labels may be detected using known techniques.

Polynucleotides, peptides or antibodies (see below) of the invention may be in substantially purified form. They may be in substantially isolated form, in which case they will generally comprise at least 90%, such as at least 95, 97 or 99% of the polynucleotide, peptide or antibody in the preparation. The substantially isolated peptides which are not peptides (as defined in the normal sense of the word) generally comprise at least 90%, such as at least 95, 97 or 99% of the dry mass of the preparation. The polynucleotide, peptide or antibody are typically substantially free of other cellular components or substantially free of other mycobacterial cellular components. The polynucleotide or peptide may be used in such a substantially isolated, purified or free form in the method or be present in such forms in the kit.

The peptide or polynucleotide may be in the form of a pharmaceutical composition which comprises the peptide or polynucleotide and a pharmaceutically acceptable carrier or diluent. Suitable carriers and diluents include isotonic saline solutions, for example phosphate-buffered saline. Typically the composition is formulated for intradermal or epidermal administration or for application by ballistic techniques. Thus the peptide or polynucleotide may be associated with a carrier particle for ballistic delivery.

The peptide of the invention can be made using standard synthetic chemistry techniques, such as by use of an automated synthesizer.

The peptide is typically made from a longer polypeptide e.g. a fusion protein, which polypeptide typically comprises the sequence of the peptide. The peptide may be derived from the polypeptide by for example hydrolysing the polypeptide, such as using a protease; or by physically breaking the polypeptide. The polypeptide is typically ESAT-6, which may have been expressed recombinantly.

The peptide can also be made in a process comprising expression of a polynucleotide, such as by expression of the polynucleotide of the invention. The expressed polypeptide may be further processed to produce the peptide of the invention. Thus the peptide may be made in a process comprising cultivating a cell transformed or transfected with an expression vector as described above under conditions to provide for expression of the peptide or a polypeptide from which the peptide can be made. The polynucleotide of the invention can be made using standard techniques, such as by using a synthesiser.

The invention also provides use of a peptide or analogue of the invention to produce an antibody specific to the peptide. This antibody or any of the antibodies mentioned herein may be produced by raising antibody in a host animal. Such antibodies will be specific to the peptide or to the substances mentioned above which bind antibodies. The peptide or substances are referred to as the 'immunogen' below. Methods of producing monoclonal and polyclonal antibodies are well-known. A method for producing a polyclonal antibody comprises immunising a suitable host animal, for example an experimental animal, with the immunogen and isolating immunoglobulins from the serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495–497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

The Identification of CD8 T Cell Epitopes

CD8 T cell epitopes of a *mycobacterium* protein may be identified by:

(i) providing to a population of cells comprising CD8 T cells (a) a peptide that comprises a mycobacterial protein sequence, or (b) an analogue of (a) that comprises a mimic of the mycobacterial protein sequence; under conditions suitable for the presentation of (a) or (b) to the CD8 T cells, and (ii) determining whether the CD8 T cells recognize (a) or (b) by detecting the expression of a substance by the T cells, the expression of the substance indicating that the T cells have recognized (a) or (b), and that (a) or (b) contain a CD8 epitope or a mimic of a CD8 epitope.

The minimal epitope which binds to the MHC molecule during recognition by the T cell may be identified, or the method may merely show that a particular peptide contains such an epitope.

In the method a peptide which comprises mycobacterial sequence can be provided to the T cell. Typically such a peptide consists of or comprises a fragment (at least 8 amino acids long, such as 10, 15, 20, 30 or more amino acids long) of a mycobacterial protein. Thus the peptide may be a natural protein, such as a *mycobacterium* protein, or a fragment thereof. The peptide may be a non-natural protein, such as a fusion protein In one embodiment pools of different peptides are provided to the T cells. If a particular pool is recognised then the peptides in each pool can be individually provided to the T cell to determine which peptide was recognised. In order to find the actual epitope which the T cell recognises (the minimal epitope) the smallest portion of *mycobacterium* sequence which the T cell recognises must be determined.

The T cell may instead be provided with an analogue of the peptide. The analogue comprises a region which mimics the mycobacterial sequence, and thus will mimic any CD8 epitope present in the mycobacterial sequence. Such a mimic of an epitope binds (and is recognised) by a T cell receptor which binds (and recognises) the epitope. Thus the mimic is capable of inhibiting the binding of the epitope to a T cell receptor which binds the epitope. In one embodiment the analogue is processed by the APC and presents the mimic bound to a MHC molecule to the T cell.

The analogue or region which mimics the epitope may have any of the characteristics of the analogue of the epitope discussed above. The analogue or region of the peptide may be related to the peptide in any of the ways the analogue of the epitope is related to the epitope, such as having homology with the peptide. Typically the analogue or region mimics the binding characteristics of the peptide, and therefore will preferably inhibit the binding of an antibody to the peptide.

Determination of whether a T cell recognizes the peptide is generally done by any of the methods discussed above in regard to the detection method provided by the invention.

Thus in the method of the invention the peptide which is presented to the T cell may been obtained by providing a *mycobacterium* protein or a protein that comprises mycobacterial protein sequence to an antigen presenting cell and allowing it to be processed to produce the peptide.

The precursor may thus itself be a polypeptide which comprises a mycobacterial sequence or an analogue of the peptide which comprises a mimic of the mycobacterial sequence. The precursor may be a fragment of ESAT-6 which is at least 8 amino acids in length.

In one embodiment the peptide or precursor is provided to the APC by providing to the APC a polynucleotide which is capable of expressing the peptide or precursor. The term 'precursor' includes such a polynucleotide. The polynucleotide may have any of the properties of the polynucleotide discussed above which is used in the vaccination or detection method, and therefore it may be present in a virus or cellular vector.

The epitopes or peptides identified in the method described above can be used to vaccinate individuals in the same manner as any of the epitopes or peptides described above. Analogues of the epitopes or peptides may be produced and used in the same manner as the analogues described above. The epitopes and peptides may also be present in the same form as any of the epitopes or peptides described above, such as being substantially isolated or purified, or be in a pharmaceutical composition with a pharmaceutically acceptable carrier or diluent, or be in a vaccine, such as a vaccine comprising the adjuvants or delivery systems discussed herein.

Administration

Any of the peptides, analogues, precursors or polynucleotides discussed above in any form or in association with any other agent discussed above is included in the termed 'vaccination agent' below. A therapeutically effective amount of such a vaccination agent may be given to a human patient in need thereof. The condition of a patient suffering from a *mycobacterium* infection can therefore be improved by administration of such a vaccination agent. The vaccination agent may be administered prophylactically to an individual who does not have a *mycobacterium* infection in order to prevent the individual becoming infected.

Thus the invention provides the vaccination agent for use in a method of treating the human or animal body by therapy. In particular the invention provides use of the vaccination agent to vaccinate against infection by a *mycobacterium*, where wherein the vaccination leads to a CD8 T cell response. The invention provides the use of the vaccination agent in the manufacture of a medicament for vaccinating against infection by a *mycobacterium*, wherein the vaccination leads to a CD8 T cell response.

Thus the invention provides a method of vaccinating an individual comprising administering the vaccination agent to the individual.

The vaccination agent is typically administered by any standard technique used for administering vaccines, such as by injection. It can be administered by ballistics techniques, for example the ballistics techniques which have been used to deliver nucleic acids. EP-A-0693119 describes ballistics techniques which can be used to administer the vaccination agent.

The vaccination agent may be in the form of a pharmaceutical composition which comprises the vaccination agent and a pharmaceutically acceptable carrier or diluent. Suitable carriers and diluents include isotonic saline solutions, for example phosphate-buffered saline. Typically the composition is formulated for parenteral, intravenous, intramuscular, subcutaneous, transdermal or oral administration.

The dose of vaccination may be determined according to various parameters, especially according to the substance used; the age, weight and condition of the patient to be treated; the route of administration; and the required regimen. A physician will be able to determine the required route of administration and dosage for any particular patient. A suitable dose may however be from 0.001 to 1000 μg, for example from 0.01 to 100 μg or 0.1 to 10 μg of the vaccination agent.

In the case of vaccination agents which are polynucleotides transfection agents may also be administered to enhance the uptake of the polynucleotides by cells. Example of suitable transfection agents include cationic agents (for example calcium phosphate and DEAE-dextran) and lipofectants (for example lipofectam™ and transfectam™).

When the vaccination agent is a polynucleotide which is in the form of a viral vector the amount of virus administered is in the range of from $10^4$ to $10^8$ pfu, preferably from $10^5$ to $10^7$ pfu, more preferably about $10^6$ pfu for herpes viral vectors and from $10^6$ to $10^{10}$ pfu, preferably from $10^7$ to $10^9$ pfu, more preferably about $10^8$ pfu for adenoviral vectors. When injected, typically 1–2 ml of virus in a pharmaceutically acceptable suitable carrier or diluent is administered.

The following Examples illustrate the invention:

EXAMPLE 1

Determination of CD8 T Cell Epitopes

The sequences of ESAT-6 and antigens 85A, 85B, and 85C of *M. tuberculosis* were scanned with allele-specific peptide motifs for the HLA class I types HLA-A2, HLA-B7, HLA-B8, HLA-B35, HLA-B52, and LA-B53. The seven congruent sequences found in ESAT-6 are shown in Table 1. No sequences congruent with HLA-B7, HLA-B35, and HLA-B53 were predicted to be present in ESAT-6.

TABLE 1

Peptides from ESAT-6

| HLA class I allele | Peptide motif | | Peptide Sequence | Position |
|---|---|---|---|---|
| HLA-A2 | -L/I/M----V/L/I | A | GIEAAASAI | 10-18 |
| | | B | AIQGNVTSI | 17-25 |
| | | C | LLDEGKQSL | 28-36 |
| | | D | ELNNALQNL | 64-72 |
| | | E | AMASTEGNV | 82-90 |
| HLA-B8 | --K-K--L/I | F | EQKQSLTKL | 31-39 |
| HLA-B52 | -Q----I/V | G | LQNLARTI | 69-76 |

A total of 49 peptides congruent with the motifs were synthesized on solid phase on a synthesizer (Zinsser, Frankfurt) using fluorenylmethoxy-carbonyl chemistry. Purity was confirmed by HPLC. These candidates epitopes were then sorted into pools according to HLA class I alleles and used to stimulate peripheral blood mononuclear cells (PBMCs) from subjects with the corresponding HLA class I allele. In vitro-expanded populations of peptide-specific T cells (STCL's made as described below) were then detected with two different assays of effector function. In a preliminary study using the standard $^{51}$Cr release CTL assay we detected low levels of lytic activity against some peptide pools, but responses from the few remaining cells were too weak to define epitopes. We therefore adapted a more sensitive enzyme-linked immunospot (ELISPOT) technique for detecting single cell interferon γ (IFN-γ) secretion. We calibrated this assay against the $^{51}$Cr release CTL assay and found it an order of magnitude more sensitive for detecting low numbers of cultured human CD8 peptide-specific T cells. The following experiments have been performed using the ELISPOT assay.

EXAMPLE 2

The Patients Used in the Study 39 adult patients and contacts with suitable HLA types were studied. Most subjects originated from the Indian subcontinent, Africa, or northern Europe. The number of patients with different clinical types of disease, as well as the number of healthy contacts, are listed in Table 2.

TABLE 2

Numbers of healthy contacts and patients with different types of clinical disease

| Clinical phenotype | Subjects, n |
|---|---|
| Pulmonary (active) | 8 |
| Pulmonary (inactive) | 6 |
| Pleural | 2 |
| Lymphadenitis | 4 |
| Osteoarticular | 5 |
| Miliary | 1 |
| Gastrointestinal | 1 |
| Epididymo-orchitis | 1 |
| Healthy contacts | 11 |

Most subjects were tuberculin skin test positive. All contacts except one who was not tested, had a positive Heaf test of grade 2 or more. All patients had at least 5 mm of cutaneous induration in response to intradermal injection with 1 tuberculin unit of purified protein derivative, except four who were not tested and four who were negative (three with old inactive pulmonary tuberculosis and one with active milliary disease). The distribution of each of the 6 HLA class I alleles for which we tested peptide pools was as follows: HLA-A2 was present in 26 subjects, HLA-B8 in 7 subjects, HLA-B7 in 6 subjects, HLA-B35 in 2 subjects, HLA-B52 in 2 subjects, and HLA-B53 in 2 subjects.

Each subject was tested against the peptide pool (or pools if the subject had more than one suitable HLA class I allele) once only. Repeat blood samples were obtained and further testing carried out only if the donor had responded on the first occasion.

NPH54 was diagnosed with tuberculosis on the basis of clinical symptoms, acute erythema nodosum and mediastinal lymph-adenopathy. Tuberculin skin test showed 25 mm induration 48 hr after intradermal injection of 1 tuberculin unit of purified protein derivative. In addition, a very high antibody titer of >1/6,250 in response to the 16 kDa antigen of *M. tuberculosis*, helped to confirm active infection (6). For NPH97, the tuberculin skin test was positive and culture of a proximal phalangeal bone biopsy of the affected hand on Lowenstein-Jensen medium grew *M. tuberculosis*.

Tissue Typing

Subjects were HLA typed serologically. NPH54, NPH97, WB, Akiba, and PG were additionally typed by amplication refractory mutation system (ARMS)-PCR using sequence-specific oligonucleotide primers (7).

EXAMPLE 3

Techniques

ELISPOT Assay for IFNγ.

Ninety-six-well polyvinylidene difluoride (PVDF)-backed plates (Millipore) precoated with the anti-IFN-γ mAB 1-D1K at 15 μg/ml (MACBTECH, Stockholm) were washed with RPMI medium 1640 and blocked with R10 for 1 hr at room temperature. Short-term cell lines (STCLs), CTL lines, or clones were washed two times in RPMI medium 1640, resuspended in R10, and dispensed at known input cell numbers per well in duplicate wells. Peptide was added either directly to the supernatant at a final concentration of 2 μM (free peptide) or presented on a B cell line (BCL) repulsed with 10 μM peptide for 1 hr at 37° C., and then washed three times in R10 Plates were incubated for 12 hr at 37° C., in 5% $CO_2$/95% air. After washing six times with phosphate buffered saline (PBS)/0.05% Tween 20 to remove cells, plates were incubated for 3 hr with the second biotinylated anti-IFN-γ mAB 7-B6-1-biotin at 1 µg/ml (MABTECH). A further wash, as above, was followed by incubation with a 1:1,000 dilution of streptavidin-alkaline phosphatase conjugate for 2 hr. After another wash, chromogenic alkaline phosphatase substrate (Bio-Rad) was added to the wells, and 30 min later plates were washed with tap water. After drying, spot-forming cells (SFC) were counted under X20 magnification. For ex vivo ELISPOT assays, 500,000 freshly isolated uncultured-PBMCs were used per well. Responses were considered significant if a minimum of 10 SFCs were present per well and, additionally, this number was at least twice that in control wells.

Generation of CD8$^+$ T Cell Lines.

STCLs were generated as described (4). Briefly PBMCs separated from whole blood were prepulsed with 30–50 µM peptide for 1 hr in a cell pellet and then diluted up to 1×10$^6$ cells/ml in RPMI medium 1640 supplemented with 10% pooled heat-inactivated human AB serum (R10) and 25 ng/ml rhIL-7 R & D Systems), and seeded at 200 µl per well in a U-bottomed 96-well plate. Lymphocult-T (Biotest, Dreiech, Germany) was added to 10% of each well at regular intervals. STCLs were assayed at day 14, Lines 3-9, 3-10, and 3-20 were generated from individual STCLs by two rounds of restimulation (on days 14 and 21) with autologous peptide-pulsed irradiated BCL at a 1:3 feeder:responder ratio. Line 4-1 was generated by pooling four G specific STCLs (originally established with CD4-depleted PBMCs), followed by restimulation with peptide-pulsed autologous BCL.

Generation of CD8$^+$ T Cell Clones.

Enumeration of IFN-γ SFCs after CD4 and CD8 depletions indicated that the frequency of CD8 G specific T cells in NPH54-derived monospecific lines 3-9 and 3-20 was I 44 and I 67 CD8 T cells, respectively. This indicated that for T cells seeded at one cell per well, 1.5–2.3 specific clones should be generated per 100 wells seeded. This quantitative data guided our cloning procedure: for each line, 240 wells were seeded at one cell per well (following CD4 depletion). Cloning mix consisted of three-way mixed lymphocyte reaction. 10% Lymphocult-T phytohemagglutinin at 1 µg/ml, and G pulsed autologous irradiated washed BCL, with a total of 100,000 feeders per well. Clones were screened in ELISPOT assays and three G specific clones were subsequently recovererd from line 3-9 and two from line 3-20. Clones were maintained by peptide-pulsed autologous irradiated BCL restimulation and supplementation with 10% Lymphocult-T and rhIL-7 at 25 ng/ml.

$^{51}$Cr Release Cytotoxicity Assays.

Standard chromium release assays were performed as described (8). In brief BCLs were labelled with 100 mCi$^{51}$Cr (Amersham), washed in RPMI medium 1640, and then pulsed with peptide as above and plated out at 5,000 cells per well. CTL, R10, or 5% Triton X-100 were added. Test well were in duplicate, other wells in quadruplicate. Plate were incubated for 5 hr at 37°, in 5% CO$_2$/95% air and harvested supernatant read on filtermats in an LKB 1205 beta-plate scintillation counter (Wallac, Gaithersburg, Md.). Background $^{51}$Cr release was less than 20%. Percent lysis was calculated from the formula 100×(E−m)/(T−M), where E is the experimental release, M is the spontaneous release, and T is the maximal release.

Specific Cell Depletions.

CD4 and CD8 T cells were depleted by 30-min incubation with anti-CD4 or anti-CD8 mAbs conjugated to ferrous beads, DYNABEADS M-450, (Dynal, Oslo) in 500 µl of R10 on ice. Following dilution of up to 5 ml in R10, the conjugate-coated cells were removed by a magnetic field. CD8 T cell depletions were highly effective and were not toxic, because there was no detectable loss of viability in the depleted population and responses of antigen 85-specific CD4 T cell lines were unaffected by depletion.

Recombinant Vaccinia Virus Construction.

Construction of the rVV is described in (9). In brief, the amplification product of the ESAT-6 gene obtained by PCR using the plasmid template pAA249 (P. Andersen, Staatens Seruminstitut, Copenhagen-S, Denmark) was cloned into plasmid p1108-tPA to create p1108-tPA-ESAT-6. Homologous recombination into the thymidine kinase locus of vaccinia strain WR with cationic lipid transfection was followed by selection of rVV using mycophenolic acid. A second negative control rVV was also constructed by using p 1108 minus the coding sequence. Recombinants were verified by sequencing and expression confirmed by PCR and capture ELISA.

EXAMPLE 4

Identification of ESAT-6-Specific Effector T Cells Direct from Peripheral Blood.

Two CD8 epitopes in ESAT-6 were identified. The T cells from donor NPH54, who had tuberculosis mediastinal lymphadenitis, recognized peptides corresponding to both of these epitopes. Uncultured PBMCs isolated at the time of the diagnosis from NPH54, who has HLA-B52 and HLA-A2.01, secreted IFNγ in response to an ESAT-6 derived peptide pool for these class I alleles in an ex vivo ELISPOT assay. The mean number of IFNγ SFCs enumerated from 5×10$^5$ PBMCs in duplicate wells was 19 for the ESAT-6 peptides compared with 2 in the control wells with no peptide. A subsequent assay tested freshly isolated PBMCs against each of the individual peptides within the responding pools; IFNγ SECs were detected in response to peptides E and G, whose sequences were congruent with the HLA-B52 and HLA-A2.01 peptide motifs, respectively. The frequency of E (1:50,000) and G (1:23,000) specific IFNγ SECs is of the same order of magnitude as SFCs for HLA-A2.01-restricted influenza matrix epitope M1 58–66 (1:14,000) (FIG. 1A). Unrestimulated PBMCs from a second donor, NPH97, with tuberculosis osteomyelitis, also recognized the G peptide. This patient also has HLA-B52 and HLA-A2.01, and the magnitude of the G specific response was similar to the response to the HLA-A2-restricted influenza matrix epitope. Single cell IFNγ release by freshly isolated T cells in these short 12-hr ex vivo assays, employing no stimulus other than cognate peptide, indicated that these cells are highly likely to be circulating activated effector T cells (2).

We have identified CD8 HLA class I-restricted T cells specific for epitopes in the *M. tuberculosis* prot in ESAT-6 in 4 of 39 infected individuals. This is almost certainly an underestimate of the actual prevalence of *M. tuberculosis* specific CD8 CTL in infected individuals for the following reasons. First, we limited the search to epitopes restricted through six HLA class I alleles. Second, of the very large number of antigens secreted by *M. tuberculosis*, we studies only two. And third, *M. tuberculosis* specific CD8 CTL are more likely to be found in draining lymph nodes or at the site of infection rather than in the peripheral circulation. Nevertheless, the frequencies of circulating ESAT-6 specific effectors in the peripheral blood of NPH54 approximates to that for an influenza virus epitope. This relatively high frequency of CTL effectors specific for a single bacterial epitope is comparable to that found in malaria, a protozoal disease, where there is substantial indirect evidence for a protective role for *Plasmodium falciparum* specific CTL (8). ESAT-6 specific effector among uncultured PBMCs were detectable in the ex vivo ELISPOT assay in NPH54 with tuberculous lymphadenitis and in NPH97 with tuberculous osteomyelitis. For the common HLA class I allele, HLA-A2, the number of subjects studied is sufficient to permit a preliminary comparison of the prevalence of responders between the different clinical subgroups. For donors with HLA-A2, E specific IFN-γ secretion in freshly isolated PBMCs of STCLs was observed in 1 of 7 healthy contacts and 2 of 3 patients with lymphadenitis, but in none of 12 patients with other more disseminated forms of disease (pulmonary, pleural, and gastrointestinal). This distribution of responses suggests that response to ESAT-6 may be associated with an immune response capable of containing *M. tuberculosis*.

The ELISPOT assay for IFN-γ release may measure an effector function of more protective relevance than the $^{51}$Cr release cytotoxicity assay. IFN-γ, a potent activator of macrophages, is essential for resistance to *M. tuberculosis* infection in mice (10, 11), whereas recent studies in perforin gene and Fas receptor gene knockout mice indicate that the lytic activity of CD8 T cells is not required to control virulent *M. tuberculosis* infection (12). Moreover, humans homozygous for a point mutation in the IFN-γ receptor 1 gene, in whom cell surface expression of this receptor is absent, are highly susceptible to fatal disseminated mycobacterial infection (13), and human T cell derived IFN-γ has recently been reported to inhibit the intracellular growth of *M. tuberculosis* (Zhang, M., Gong, J., Lin, Y, Boylen, C. T & Barnes, P. F. American Association of Immunologists Joint Meeting, Jun. 2–6, 1996, New Orleans, La.). CD8 CTL derived IFN-γ may be especially important both for cells lacking MHC class II molecules, e.g. in the lung (14) and for macrophages where mycobacteria can evade recognition during chronic infection by sequestering their antigens away from sensitized CD4 T cells (15). Morever, infection of murine macrophage cell lines with live *M. tuberculosis* has recently been shown to down-regulate MHC class II expression while simultaneously enhancing the presentation of exogenous soluble antigen through the MHC class I antigen processing pathway (16).

EXAMPLE 5

ESAT-6 Epitope-Specific T Cells are CD8.

G specific T cell lines were generated from NPH54 and NPH97 PBMCs. Depletion experiments demonstrated that-the G specific T cells are CD8 (FIG. 1B. Enumeration of IFN-γ SFCs in a 12 hr ELISPOT assay for IFN-γ with cell line 3-20 from donor NPH54 was performed and is shown. After depletion of CD4 or CD8 cells, 20,000 cells were added to each of a pair of duplicate wells and peptide G was added to a final concentration of 2 μM: the mean number of SFCs is shown in FIG. 1B. No SFCs were observed in the absence of peptide. CD8 cell depletion completely abrogates the response. Similar results were obtained with cell line 3-9. Similar depletion studies on E specific STCLs from donor WB, a healthy contact with HLA-A2.01, confirmed that these E specific T cells are also CD8 (FIG. 1C). After magnetic depletion of CD4 or CD8 cells, 20,000 cells were added to each of a pair of duplicate wells in a 12 hr ELISPOT assay and peptide added at 2 μM to the supernatant. The mean number of IFNγ SECs for each pair of wells is shown in FIG. 1C. CD4-depleted E specific STCLs from donor NPH43, a patient with lymphadenitis (class I HLA haplotype. HLA-A2.01, HLA-A29, HLA-B7, and HLA-B51), recognized peptide presented through HLA-A2.01 on E-repulsed HLA-A2.01 matched heterologous BCL. Ninety eight IFNγ SFCs were enumerated in response to the E-pulsed BCL, compared with 48 IFNγ SECs for the unpulsed control BCL; the high backgrounds are probably due to alloresponse (24). Responses to E were transient and often undetectable in PBMCs from subsequent blood samples drawn later in the course of therapy.

No CD8 epitopes were identified among any of the 42 peptides from antigens 85A, 85B, or 85C. Despite stimulation in vitro with nonamer peptides, the resultant STCLs were all CD4. Interestingly, certain peptides elicited IFN-γ secretion by freshly isolated uncultured CD4 cells in 12-hr ex vivo ELISPOT assays.

EXAMPLE 6

ES12-Specific CD8 T Cells are MHC Class I-Restricted and Recognize Endogenously Processed Antigen.

The epitope G was further characterized with G specific lines and clones. T cell recognition of peptide had until now relied on presentation of G on autologous cells by adding free peptide to the ELISPOT assay supernatant. To demonstrate HLA class I restriction, G peptide was presented to clones derived from NPH54 with G-prepulsed BCL matched (from Akiba) or mismatched (from donor PG) at B52; only HLA-B52-matched G prepulsed BCL were recognised by cells pooled from clones 3-1, 3-15, and 3-98. The matched BCL from Akiba are homozygous for HLA-A24 and HLA-B52. The mismatched BCL from PG are HLA-A2.01, HLA-A3, HLA-B7 and HLA-B51. Assays were performed in duplicate wells with 5,000 T cells and 50,000 B cells per well. Only the pair of duplicate wells with G-pulsed HLA-B52 matched targets are positive: the spots were so numerous that they appeared confluent. G-specific lines raised from NPH97's PBMCs were similarly confirmed to be HLA-B52 restricted (data not shown).

To show that the G-specific CD8 T cell clones were capable of recognizing endogenously processed antigen, autologous BCL, infected with vaccinia virus recombinant for ESAT-6 (rVV-ESAT-6) or a control lacking the ESAT-6 sequence, were used to stimulate cytokine release. BCL were infected the night before with the respective recombinant viruses at a multiplicity of infection (m.o.i) of 7 plaque forming units per cell in serum free medium; after 90 min, cells were diluted up to 1 million/ml in R10 and incubated overnight. Infected BCL (100,000) were then added to each well along with 5,000 cloned T cells. Only clones 3-1, 3-15, and 3-98 incubated with the ESAT-6 recombinant vaccinia-infected BCL secreted IFN-γ in the ELISPOT assay. 3-15 gavie in excess of 450 SFCs. The results with the other two clones, 3-1, 3-98, were so strongly positive that the spots were confluent.

EXAMPLE 7

*M. tuberculosis* Antigen-Specific CD8$^+$ T Cells are Cytolytic.

Figure 2:
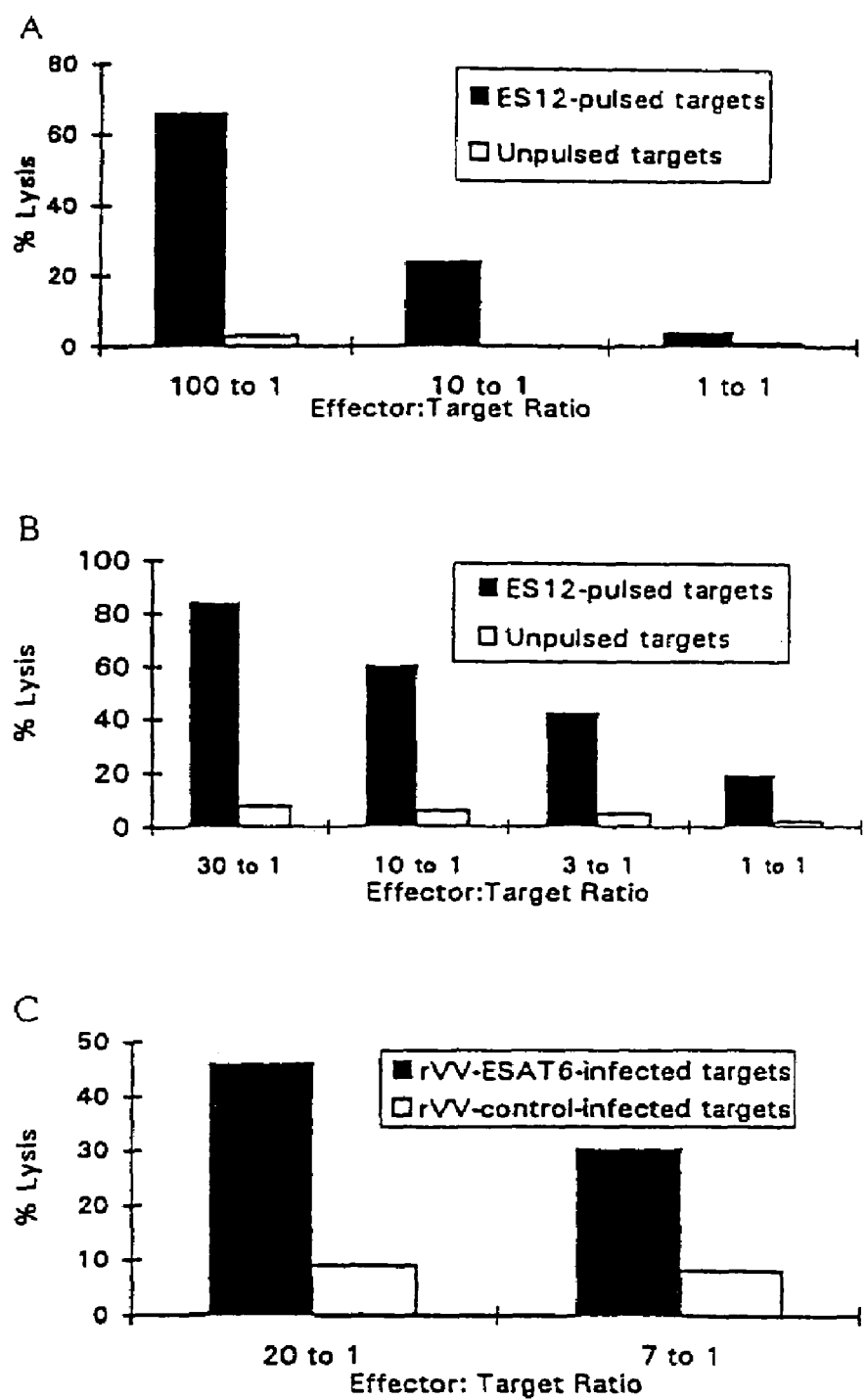
FIG. 2(A) shows peptide G specific cytolytic activity of CTL line 4-1 from NPH54.
FIG. 2(B) shows peptide G specific cytolytic activity of a CTL line from NPH97.
FIG. 2(C) shows lysis of HLA-B52 matched heterologous targets (Akiba BCL) expressing endogenously processed ESAT-6.

By using a sensitive measurement of cytokine release, we characterised CD8 T cells specific for G. We now returned to conventional $^{51}$Cr release assays to test whether these cells were also capable of lytic activity. This was confirmed over a broad range of effector-target ratios for CD8 T cell lines from both NPH54 and NPH97 using G-pulsed heterologous HLA-B52 matched BCL as targets (FIGS. 2A and B). Peptide-specific lysis was detectable even when the peptide prepulse concentration was titrated as low as 1 nM (data not shown). FIG. 2(A) shows G specific cytolytic activity of CTL line 4-1 from donor NPH54 in a 5 hr $^{51}$Cr release cytotoxicity assay. Peptide specific lysis titrated downwards with diminishing effector to target cell ratio, and nonspecific lysis of unpulsed targets was less than 5%. Target cells were heterologous HLA-B52 matched BCL (homozygous typing line, Akiba: HLA-A24. HLA-B52), prepulsed with 10 μM G. FIG. 2(B) shows G specific cytolytic activity of a CTL line from donor NPH97 in a 5 hr $^{51}$Cr release cytotoxicity assay. The CTL line was generated by restimulation of 14 days STCLs cultured as described above with G pulsed, washed, irradiated autologous BCL. Peptide specific lysis titrated downwards with each 3 fold diminution in effector-to-target cell ratio, and nonspecific lysis of unpulsed targets was less than 5%. Target cells were heterologous HLA-B52 matched BCL (Akiba) prepulsed with 10 μM of G.

Finally, to establish whether G-specific CTL could also kill targets expressing endogenously processed antigen, we demonstrated HLA-B52-restricted lysis of heterologous HLA-B52-matched targets (Akiba BCL) infected with rVV-ESAT-6 (FIG. 2C). Targets were infected with rVV-ESAT-6 and rVV control and were labelled with $^{51}$Cr the following day. CTL line 4-1 raised against G specifically lysed the rVV-ESAT-6 infected targets; lysis of rVV control infected targets was below 10%.

CONCLUSIONS

The observation that G specific T cell lines and clones recognize target cells infected with vaccinia virus recombinant for ESAT-6 indicates that this antigen can be endogenously processed through the MHC class I antigen processing pathway, resulting in the presentation of the epitope G through HLA-B52. Because responses to the *M. tuberculosis* specific peptide ES12 were elicited from freshly isolated, unrestimulated lymphocytes in an ex vivo assay, CD8 T cells must have been primed through recognition of processed antigen in vivo. This study thus provides evidence that in humans an *M. tuberculosis* antigen is naturally processed in vivo through the MHC class I pathway leading to the induction of MHC class I restricted effector T cells. Further support comes from preliminary data showing that human macrophages infected with *M. tuberculosis* in vitro are recognized by G specific HLA-B52 restricted CTL that suppress mycobacterial growth (data not shown).

Murine models, including studies with $β_2$-microglobulin gene knockout mice (17), TAP-1 null mutant mice (16), and adoptive transfer experiments with HSP-65 immunized mice (18) show that CD8 CTL are essential for protection against *M. tuberculosis* infection. CD8 T cells also constitute a crucial effector mechanism in the protective immunity conferred by DNA vaccination against tuberculosis (19, 20). It has therefore been important to establish whether MHC class I restricted CD8 CTL play a role in *M. tuberculosis* infection in humans, for, if so, their induction could guide the rational design of subunit vaccines. However, it has proved very difficult to identify these cells in humans (21, 22). Indeed, the recent identification of human CD1 restricted CD8 T cells specific for *M. tuberculosis* non peptide antigens has led to the suggestion that disruption of CD1-mediated antigen presentation may account for the enhanced susceptibility of $β_2$-microglobulin gene knockout mice to *M. tuberculosis* infection (23). However, this study demonstrates the presence of classical MHC class I restricted CD8 CTL specific for an *M. tuberculosis* protein antigen in infected individuals. These cells circulate at a relatively high frequency in peripheral blood and freshly isolated, unrestimulated cells rapidly display effector function within 12 hr of antigen contact. Induction of MHC class I restricted peptide specific CD8 CTL with new generation CTL inducing vaccines is now feasible. The phenotype and specificity of the cells identified here not only endorses efforts to develop CTL inducing vaccines against tuberculosis but also supports the candidacy of ESAT-6 as a component of such vaccines.

EXAMPLE 8

The Identification of Further Epitopes

Figure 5:
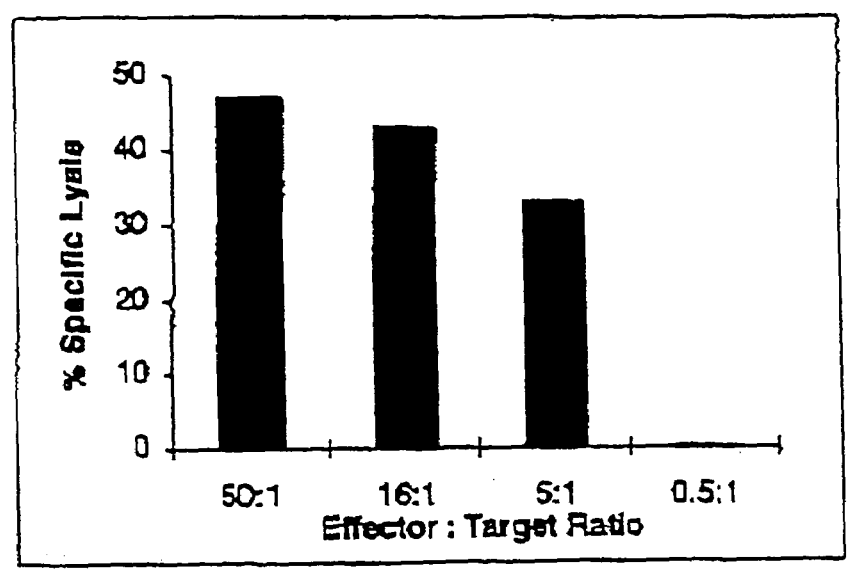
FIG. 5 shows lysis of HLA-A68.02 matched heterologous BCL by CTL from NPH130.
Figure 6:
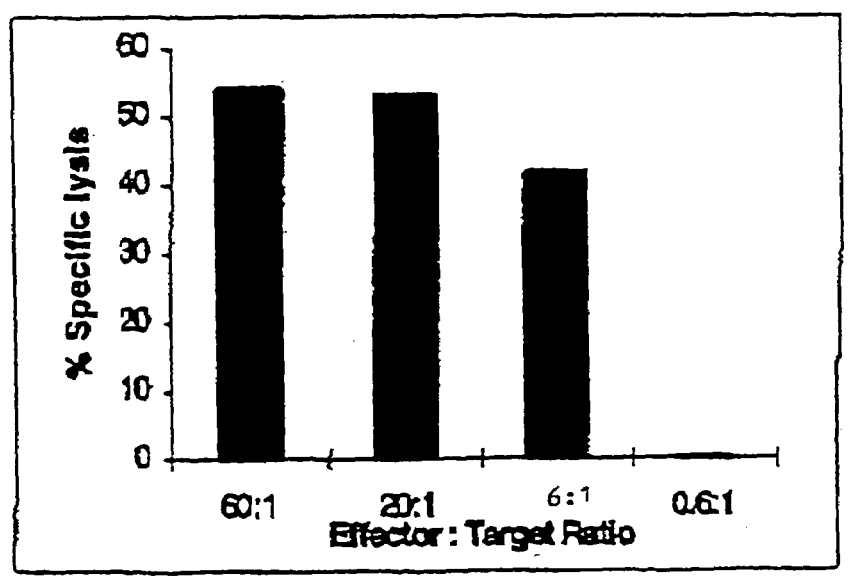
FIG. 6 shows lysis of autologous BCL by CTL from NPH172.

The ELISPOT assay was also used to show that the minimal epitope NVTSIHSLL is recognised by CD8+ CTL lines from 2 different individuals: one a patient with sputum smear positive pulmonary TB (NPH130, FIG. 5) and the other, remarkably, a healthy household contact (NPH172, FIG. 6). CTL lines from both subjects demonstrate vigorous cytolytic activity.

NPH 144, a patient with miliary and meningeal tuberculosis recognizes two different epitopes. CD8+CTL lines specific for the 15mer NLARTISEAGQAMAS (SEQ ID NO:6) are strongly cytolytic. The minimal epitope, RTISEAGQAM (SEQ ID NO:9), has been defined. T cell lines have been generated against this epitope from *M. tuberculosis*-infected individuals and these lines have been shown to be CD8 positive (by immunomagnetic depletion prior to interferon-gamma ELISPOT assay) and cytolytic (in chromium release cytotoxicity assays). The epitope is restricted through HLA-B5702, as evidenced by T cell recognition of HLA-B5702- matched, but not mismatched, peptide-pulsed B cell lines in chromium release and interferon-gamma ELISPOT assays. CD8 T cells specific for this epitope have been detected at high frequencies directly from the peripheral blood of *M. tuberculosis*-infected individuals in ex vivo interferon-gamma ELISPOT assays.

A second CD8+ T cell epitope is also recognized by NPH144. This epitope is contained within the 15mer TATELNNALQNLART (SEQ ID NO:5) and is represented by TATELNNAL (SEQ ID NO:8). T cell lines and clones have been generated against this 9mer peptide from *M. tuberculosis*-infected individuals and these lines have been shown to be CD8 positive (by immunomagnetic depletion prior to interferon-gamma ELISPOT assay and FACS analysis) and cytolytic (in chromium release cytotoxicity assays). The epitope is restricted through HLA-B3503, as evidenced by T cell recognition of HLA-B3503-matched, but not mismatched, peptide-pulsed B cell lines in chromium release and interferon-gamma ELISPOT assays. CD8 T cells specific for this epitope have been detected at high frequencies directly from the peripheral blood of *M. tuberculosis*-infected individuals in ex vivo interferon-gamma ELISPOT assays and by peptide-MHC tetramers.

EXAMPLE 9

ESAT-6-specific CD8+ Effector T Cells Circulate at High Frequencies in Some *M. tuberculosis*-infected Individuals.

Figure 3:
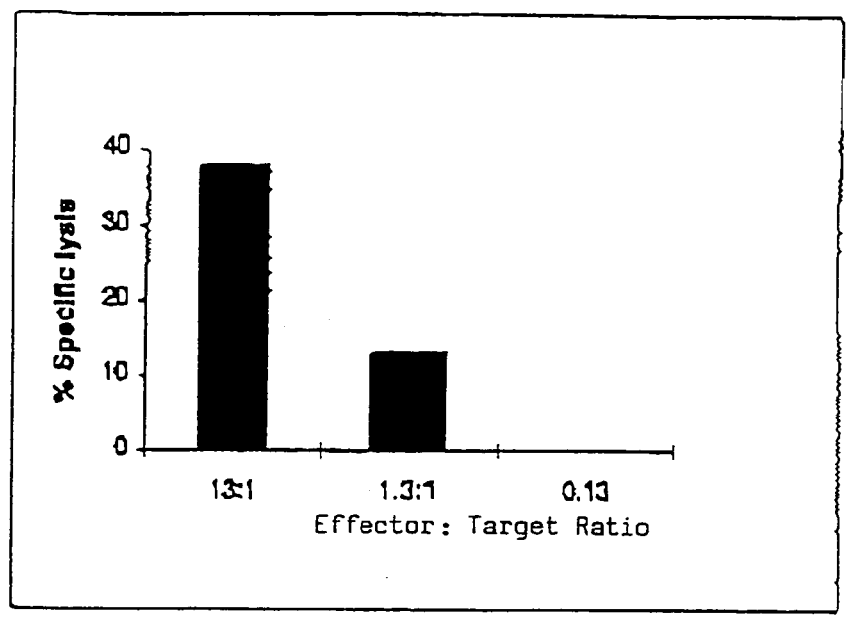
FIG. 3 shows lysis of autologous macrophage targets by CTL from NPH144.
Figure 4:
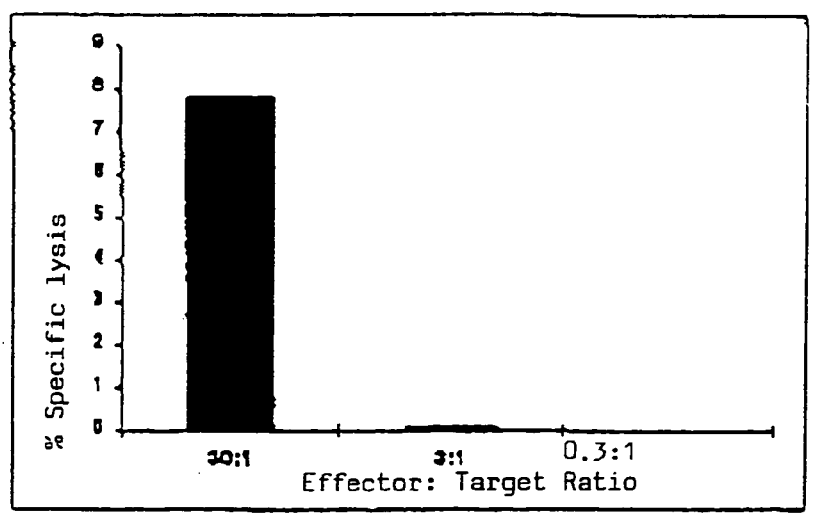
FIG. 4 shows lysis of HLA-A11.01 matched heterologous BCL by CTL from NPH144

In an ex-vivo 9-hr ELISPOT assay with freshly isolated PBL from NPH 144 responses to peptide ES15 (TATELN-NALQNLART, SEQ ID NO:5) and ES13 (NLAR-TISEAGQAMAS, SEQ ID NO:6) are found within 9-hrs of antigen contact (FIGS. 3 and 4). This ex-vivo response is abrogated by CD8 depletion with Dynabeads. The frequency of circulating T cells specific for ES15 in NPH144 ranges from 1/500–1/3,000. The mild diminution in the response with CD4 depletion indicated that peptide ES15 may also be a target of IFN-γ secreting CD4+ T cells in NPH144, as it is in many other tuberculosis patients and contacts.

T Cells Specific for Peptide ES15 were Found to Infiltrate the Pus of a Tuberculosis Cold Abscess.

After 15 months anti-tuberculous chemotherapy, NPH144 remains clinically generally well except for a recurrent pus-filled cold abscess at the site of the left supraclavicular lymph nodes. Aspirated pus from this site is AFB smear negative and culture negative. The pus consists of lymphocytes and neutrophils; 90% of these infiltrating white cells are apoptosed. An ex vivo ELISPOT assay with the surviving cells from the aspirated pus shows the presence of ES15 peptide-specific IFN-γ secreting T cells in the pus.

Identification of the Minimal Epitope within the Peptide SGSEAYQGVQQKWDA

Within the 15mer peptide SGSEAYQGVQQKWDA (SEQ ID NO:7), the minimal epitope, AYQGVQQKW (SEQ ID NO:10) has been defined. T cell lines have been generated against this epitope from *M. tuberculosis*-infected individuals and these lines have been shown to be CD8 positive (by immunomagnetic depletion prior to interferon-gamma ELISPOT assay) and cytolytic (in chromium release cytotoxicity assays). The epitope is restricted through HLA-A24, as evidenced by T cell recognition of HLA-A24-matched, but not mismatched, peptide-pulsed B cell lines in chromium release and interferon-gamma ELISPOT assays. CD8 T cells specific for this epitope have been detected at high frequencies directly from the peripheral blood of *M. tuberculosis*-infected individuals in ex vivo interferon-gamma ELISPOT assays. Additionally, a second CD8 epitope exists within the 15mer SGSEAYQGVQQKWDA (SEQ ID NO:7). This epitope is restricted through HLA-B44, as evidenced by T cell recognition of HLA-B44-matched, but not mismatched, peptide-pulsed B cell lines in interferon-gamma ELISPOT assays. The identity of the precise minimal epitope is under investigation and, on the basis of the HLA-B44 peptide motif, is very likely to be either SEAYQGVQQ (SEQ ID NO:11) or SEAYQGVQQK (SEQ ID NO:12).

Discussion

We have identified 8 CD8 T cell epitopes in ESAT-6. These epitopes are restricted through HLA-B52 (for LQN-LARTI, SEQ ID NO:2), A2 (for AMASTEGNV, SEQ ID NO:1), A68.02 (for NVTSIHSLL, SEQ ID NO:3) B3503 (for TATELNNAL, SEQ ID NO:8), B5702 (for RTISEAGQAM, SEQ ID NO:9), A24 (for AYQGVQQKW, SEQ ID NO:10) and B44 (for the second epitope present in SGSEAYQGVQQKWDA, SEQ ID NO:7). ESAT-6, only 95 amino acids in length, is thus extraordinarily rich in CD8+ CTL epitopes. Some of these epitopes moreover overlap with certain human CD4+ epitopes (e.g. peptide ES15).

The frequency of ESAT-6-specific CD8+ T cells is very high in some individuals and these cells are capable of rapid effector function in short duration ELISPOT assays for IFN-γ.

We have shown that ESAT-6-specific CD8+ CTL can affect an unusual delayed suppression of the growth of *M. tuberculosis* in vitro but the role of these CD8+ CTL in humans in vivo is not known. One of our subjects, NPH130, a healthy household contact, has a high frequency (1/1,000 PBL) of CD8+ CTL specific for the HLA-A68.02 restricted epitope NVTSIHSLL (SEQ ID NO:3), as demonstrated by ex vivo ELISPOT (FIG. 5). The presence of such a high frequency of *M. tuberculosis* specific CD8+ CTLs in an exposed but healthy individual with a clinically undetectable bacillary load raises the possibility that these T cells may, in some individuals, be associated with containment of *M. tuberculosis* in vivo.

REFERENCES

1. Devereux et al (1984) *Nucleic Acids Research* 12, 387–395.
2. Lalvani, A., et al. (1997) *J.Exp. Med* 186, 859–865.
3. Herr et al (1996) *J. Immunological Methods.* 191, 131–141.
4. Ota, K., et al. (1990) *Nature (London)* 346, 183–187.
5. Kohler and Milstein (1975) *Nature* 256, 495–497.
6. Wilkinson, R. J., et al. (1998) Ph.D. thesis (London Univ., London)
7. Krausa, P. M., et al. (1995) *Tissue Antigens* 45, 223–231.
8. Hill, A. V. S., et al. (1992) *Nature (London)* 360, 434–439.
9. Mackett, M (1995) in DNA Cloning 4: A Practical Approach, eds. Glover & Hanes, (IRL Oxford), p43.
10. Cooper, A, M., et al. (1993) *J. Exp. Med* 178, 2243–2247.
11. Flynn, J. L., et al. (1993) *J. Exp. Med* 178, 2249–2254.
12. Laochumroonvorapong, P., et al. (1997) *Infect. Immun* 65, 127–132.
13. Newport, M. J., et al. (1996) *N. Engl. J. Med* 335, 1941–1949.
14. Orme, I. M., (1997) in Host Response to Intracellular Pathogens, ed. Kaufmann, S. E. H. (Landes, Austin, Tex.), pp. 115–130.
15. Pancholi, P., et al. (1993) *Science* 260, 984–986.
16. Mazzacaro, R. J., et al. (1996) *Proc. Natl. Acad. Sci USA* 93, 11786–11791.
17. Flynn, J. L., et al. (1992) *Proc. Natl. Acad Aci USA* 89, 12013–12017.
18. Silva, C. L., Silva, M. F., Pietro, R. C. L. R. & Lowrie, D. B. (1994) *Immunology* 83, 341–346.
19. Huygen, K., et al. (1996) *Nat. Med.* 2, 893–898.
20. Tascon, R. E., et al, (1996) *Nat. Med.* 2, 888–892.
21. Turner. J & Dockrell, H. M (1996) *Immunology* 87, 339–342.
22. DeLibero, G., et al, (1988) *Eur. J. Immunol.* 18, 59–64.
23. Stenger, S., et al, (1997) *Science* 276, 1684–1687.
24. Roche, P., et al. (1994) *Infect. Immun* 62, 5319–5326.
25. Allsopp, C. E., et al (1996) *Eur. J. Immunol.* 26, 1951–9.
26. Hioe, C. E., et al (1996) *Vaccine* 14, 412–8.

The invention claimed is:

1. A method of detecting an anti-mycobacterial CD8 T cell response comprising contacting a population of CD8 T cells of a human individual with one or more peptides selected from the group consisting of SEQ ID NOS:3, 4, 7, 8, 9, 10, 11 and 12, and, optionally, one or two further peptides selected from the group consisting of SEQ ID NOS:1 and 2, wherein one or more peptides may be substituted by an analogue which binds a T cell receptor that recognizes the peptide, and determining whether CD8 T cells of the CD8 T cell population recognize the peptide(s).

2. A method according to claim 1 wherein a peptide panel is employed, wherein said panel includes peptides consisting of SEQ ID NOS:1, 2, 3, 4, 8, 9 and 10, wherein one or more peptides may be substituted by said analogue.

3. A method according to claim 1 wherein any analogue which is used is (i) at least 70% homologous, preferably at least 80% homologous, more preferably at least 90% homologous, to the entire peptide, and/or (ii) has one or more deletions at the N-terminus and/or C-terminus in comparison to the peptide, and/or (iii) has one or more conservative substitutions compared to the peptide.

4. A method according to claim 1 in which the recognition of the peptide(s) by the CD8 T cells is determined by measuring secretion of a cytokine from the CD8 T cells.

5. A method according to claim 4 in which IFN-γ secretion from the T cells is measured.

6. A method according to claim 5 in which IFN-γ secretion from the CD8 T cells is determined by allowing secreted IFN-γ to bind an immobilized antibody specific to the cytokine and then determining the presence of antibody/cytokine complex.

7. A method according to claim 1 in which the CD8 T cells are freshly isolated ex vivo cells from peripheral blood.

8. A method according to claim 1 in which CD8 T cells are pre-cultured in vitro with the peptide(s).

9. A method according to claim 1 in which the *mycobacterium* is *M. tuberculosis*.

10. A method according to claim 1 wherein the population of CD8 T cells is from an individual to whom an anti-mycobacterial vaccine has been administered.

11. A method according to claim 1 which is carried out in vitro.

12. A kit comprising one or more peptides selected from the group consisting of SEQ ID NOS:3, 8, 9, 10, 11 and 12, and, optionally, one or two further peptides selected from the group consisting of SEQ ID NOS:1 and 2, wherein one or more peptides may be substituted by an analogue which binds a T cell receptor which recognizes the peptide, and optionally a means to detect recognition of the peptide(s) by CD8 T cells.

13. A kit comprising a peptide panel, wherein said panel includes peptides consisting of SEQ ID NOS:1, 2, 3, 4, 8, 9 and 10, wherein one or more peptides may be substituted by an analogue which binds a T cell receptor which recognizes the peptide.

14. A kit according to claim 12 which includes an antibody to IFN-γ.

15. A kit according to claim 14 wherein said antibody is immobilized on a solid support and which optionally also includes a means to detect any antibody/IFN-γ complex.

16. A kit according to claim 12 which includes the means to detect recognition of the peptide(s) by CD8 T cells.

17. A kit according to claim 14 which includes the means to detect recognition of the peptide(s) by CD8 T cells.

18. A kit according to claim 15 which includes the means to detect any antibody/IFN-γ complex.

* * * * *

SEQUENCE LISTING

<160> NUMBER OF SEQ ID NOS: 17

<210> SEQ ID NO 1
<211> LENGTH: 9
<212> TYPE: PRT
<213> ORGANISM: M. tuberculosis

<400> SEQUENCE: 1

Ala Met Ala Ser Thr Glu Gly Asn Val
1               5

<210> SEQ ID NO 2
<211> LENGTH: 8
<212> TYPE: PRT
<213> ORGANISM: M. tuberculosis

<400> SEQUENCE: 2

Leu Gln Asn Leu Ala Arg Thr Ile
1               5

<210> SEQ ID NO 3
<211> LENGTH: 9
<212> TYPE: PRT
<213> ORGANISM: M. tuberculosis

<400> SEQUENCE: 3

Asn Val Thr Ser Ile His Ser Leu Leu
1               5

<210> SEQ ID NO 4
<211> LENGTH: 12
<212> TYPE: PRT
<213> ORGANISM: M. tuberculosis

<400> SEQUENCE: 4

Glu Leu Asn Asn Ala Leu Gln Asn Leu Ala Arg Thr
1               5                   10

<210> SEQ ID NO 5
<211> LENGTH: 15
<212> TYPE: PRT
<213> ORGANISM: M. tuberculosis

<400> SEQUENCE: 5

Thr Ala Thr Glu Leu Asn Asn Ala Leu Gln Asn Leu Ala Arg Thr
1               5                   10                  15

<210> SEQ ID NO 6
<211> LENGTH: 15
<212> TYPE: PRT
<213> ORGANISM: M. tuberculosis

<400> SEQUENCE: 6

Asn Leu Ala Arg Thr Ile Ser Glu Ala Gly Gln Ala Met Ala Ser
1               5                   10                  15

<210> SEQ ID NO 7
<211> LENGTH: 15
<212> TYPE: PRT
<213> ORGANISM: M. tuberculosis

<400> SEQUENCE: 7

Ser Gly Ser Glu Ala Tyr Gln Gly Val Gln Gln Lys Trp Asp Ala

```
                  1               5              10              15

<210> SEQ ID NO 8
<211> LENGTH: 9
<212> TYPE: PRT
<213> ORGANISM: M. tuberculosis

<400> SEQUENCE: 8

Thr Ala Thr Glu Leu Asn Asn Ala Leu
1               5

<210> SEQ ID NO 9
<211> LENGTH: 10
<212> TYPE: PRT
<213> ORGANISM: M. tuberculosis

<400> SEQUENCE: 9

Arg Thr Ile Ser Glu Ala Gly Gln Ala Met
1               5              10

<210> SEQ ID NO 10
<211> LENGTH: 9
<212> TYPE: PRT
<213> ORGANISM: M. tuberculosis

<400> SEQUENCE: 10

Ala Tyr Gln Gly Val Gln Gln Lys Trp
1               5

<210> SEQ ID NO 11
<211> LENGTH: 9
<212> TYPE: PRT
<213> ORGANISM: M. tuberculosis

<400> SEQUENCE: 11

Ser Glu Ala Tyr Gln Gly Val Gln Gln
1               5

<210> SEQ ID NO 12
<211> LENGTH: 10
<212> TYPE: PRT
<213> ORGANISM: M. tuberculosis

<400> SEQUENCE: 12

Ser Glu Ala Tyr Gln Gly Val Gln Gln Lys
1               5              10

<210> SEQ ID NO 13
<211> LENGTH: 9
<212> TYPE: PRT
<213> ORGANISM: M. tuberculosis

<400> SEQUENCE: 13

Gly Ile Glu Ala Ala Ala Ser Ala Ile
1               5

<210> SEQ ID NO 14
<211> LENGTH: 9
<212> TYPE: PRT
<213> ORGANISM: M. tuberculosis

<400> SEQUENCE: 14

Ala Ile Gln Gly Asn Val Thr Ser Ile
1               5
```

```
<210> SEQ ID NO 15
<211> LENGTH: 9
<212> TYPE: PRT
<213> ORGANISM: M. tuberculosis

<400> SEQUENCE: 15

Leu Leu Asp Glu Gly Lys Gln Ser Leu
1               5

<210> SEQ ID NO 16
<211> LENGTH: 9
<212> TYPE: PRT
<213> ORGANISM: M. tuberculosis

<400> SEQUENCE: 16

Glu Leu Asn Asn Ala Leu Gln Asn Leu
1               5

<210> SEQ ID NO 17
<211> LENGTH: 9
<212> TYPE: PRT
<213> ORGANISM: M. tuberculosis

<400> SEQUENCE: 17

Glu Gln Lys Gln Ser Leu Thr Lys Leu
1               5
```